(12) United States Patent
Pierre et al.

(10) Patent No.: US 8,002,940 B2
(45) Date of Patent: Aug. 23, 2011

(54) HOSE RETAINER FOR THERMAL BLANKET

(75) Inventors: Joseph Pierre, Libertyville, IL (US); Rachel Starr, Randolph, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 12/654,905

(22) Filed: Jan. 8, 2010

(65) Prior Publication Data
US 2010/0108243 A1 May 6, 2010

Related U.S. Application Data

(62) Division of application No. 11/401,957, filed on Apr. 12, 2006, now Pat. No. 7,658,756.

(51) Int. Cl.
*A41H 37/00* (2006.01)
*A44B 19/00* (2006.01)
*B29C 65/00* (2006.01)
*B32B 37/00* (2006.01)
*B32B 38/04* (2006.01)
*A47C 27/00* (2006.01)
*A47C 27/08* (2006.01)
*A47C 17/00* (2006.01)
*A61F 7/00* (2006.01)

(52) U.S. Cl. .......... 156/292; 156/66; 156/252; 156/290; 5/423; 5/714; 5/726; 607/107

(58) Field of Classification Search .................. 156/60, 156/66, 91, 92, 145, 196, 211, 221, 223, 156/226, 227, 250, 252, 290, 291, 292, 303.1; 5/421, 423, 600, 606, 707, 710, 711, 712, 5/713, 714, 724, 726; 607/96, 104, 107, 607/108, 109

See application file for complete search history.

(56) References Cited

U.S. PATENT DOCUMENTS

| | | | |
|---|---|---|---|
| 4,395,800 A | | 8/1983 | Shindelaar |
| 5,125,238 A | * | 6/1992 | Ragan et al. ............. 62/259.3 |
| 5,304,213 A | * | 4/1994 | Berke et al. ............. 607/104 |
| 5,792,224 A | * | 8/1998 | Fu et al. ............. 55/375 |

(Continued)

*Primary Examiner* — Philip C Tucker
*Assistant Examiner* — Brian R Slawski
(74) *Attorney, Agent, or Firm* — Louis Woo

(57) ABSTRACT

An inflatable convective thermal blanket is designed to have at least one section on its top surface that has securely mounted thereon at least one fluid absorbent mechanism for absorbing fluids from a subject that is placed onto the blanket, or from fluids fallen onto the blanket from other sources. The one section is configured onto the blanket in such a way that it forms a well for collecting the fluids. The fluid absorbent mechanism, which may be in the form of a pad, would absorb the collected fluid to thereby minimize evaporative and cooling effects on the subject. Instead of mounting it on top of the blanket, the fluid absorbent pad may be mounted to the underside of the blanket, with appropriate holes and/or openings provided at the fluid collecting section, so that the collected fluids are drained onto the fluid absorbent pad. To enhance the input flow of air to the blanket, as well as to enable the blanket to be flatly folded for storage or shipping, a collapsible retainer mechanism is provided at the input port(s) of the blanket. The retainer mechanism opens up to a shape that facilitates the mating of an air hose to the input port. When folded to its collapsed position, the retainer mechanism, and the input port, would lie substantially coplanarly with the blanket. When configured to the position for accepting the air hose, the retainer mechanism is positioned substantially orthogonal to the blanket.

16 Claims, 7 Drawing Sheets

U.S. PATENT DOCUMENTS

| | | |
|---|---|---|
| 6,182,704 B1 | 2/2001 | Bevacco |
| 6,228,107 B1 | 5/2001 | Arnold et al. |
| 6,309,408 B1 * | 10/2001 | Arnold et al. .......... 607/104 |
| 6,666,879 B2 | 12/2003 | Arnold et al. |
| 6,679,432 B1 | 1/2004 | Arnold |
| 2001/0012957 A1 | 8/2001 | Arnold et al. |
| 2002/0029072 A1 | 3/2002 | Arnold et al. |
| 2003/0036786 A1 * | 2/2003 | Duren et al. ............ 607/96 |

* cited by examiner

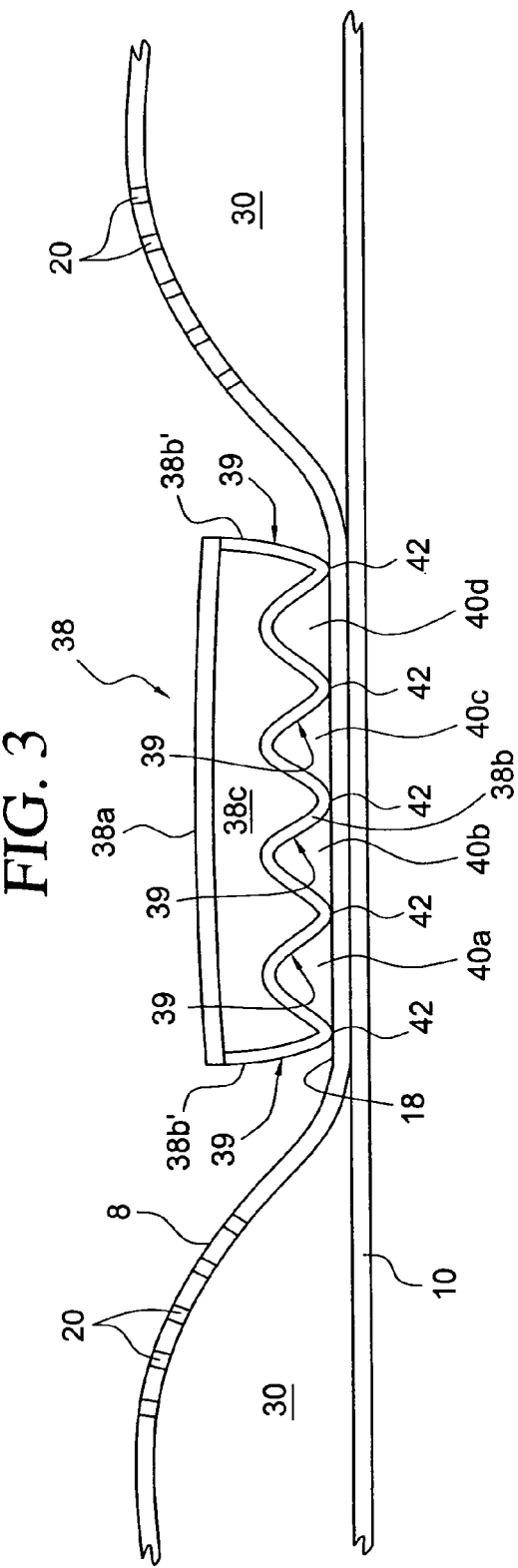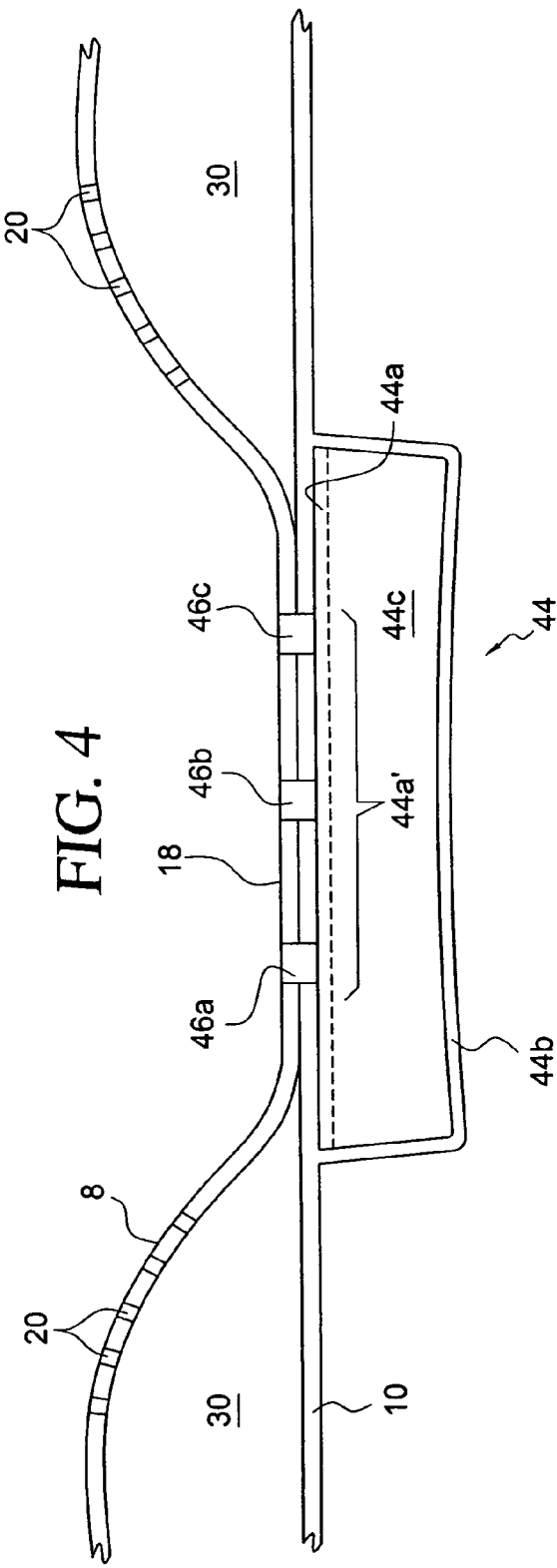

FIG. 7
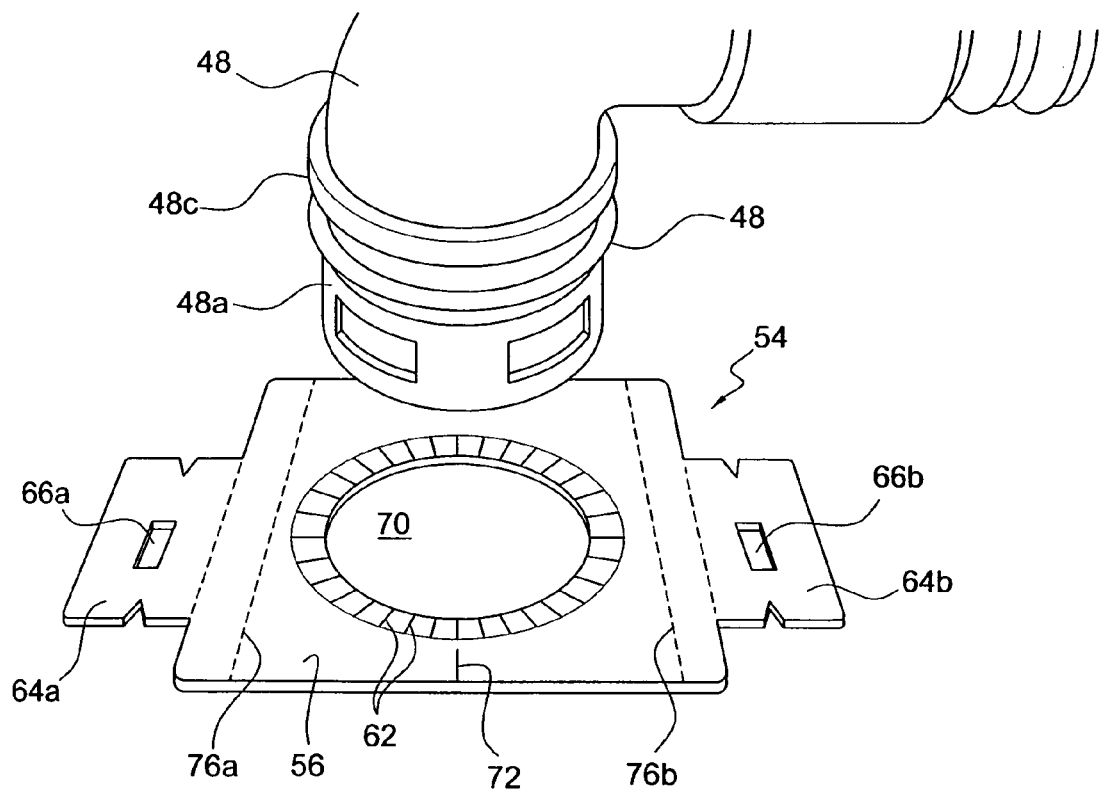
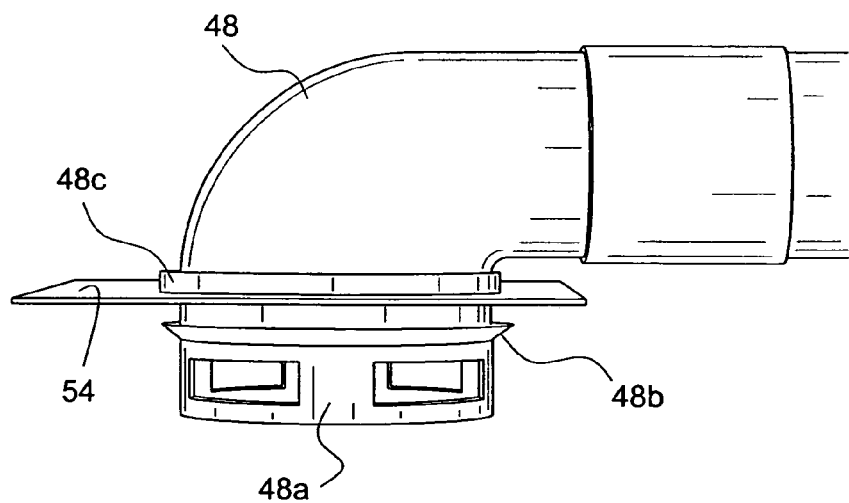
FIG. 8

HOSE RETAINER FOR THERMAL BLANKET

IDENTIFICATION OF RELATED APPLICATION

This patent application is a division of U.S. patent application Ser. No. 11/401,957 filed Apr. 12, 2006, now U.S. Pat. No. 7,658,756.

FIELD OF THE INVENTION

The present invention relates to thermal blankets, and more particularly to a fluid absorbent thermal blanket onto which a patient is placed. The invention also relates to a low profile thermal blanket made possible by a new design of the retainer mechanism at the input port of the blanket.

BACKGROUND OF THE INVENTION

An inflatable thermal blanket that is used to support a patient is disclosed in U.S. Pat. No. 6,102,936. The '936 blanket has its top layer and its bottom layer joined together at a number of point joined locations. To remove fluids that may accumulate on the blanket, drain openings are provided at the joined locations so that the fluids may be drained from the blanket onto the table or bed onto which the blanket is placed, and from there presumably to a fluid collection tray. The use of the '936 thermal blanket therefore requires that the blanket be carefully placed on the table or bed, and be positioned relative to a fluid collection tray. Alternatively, a fluid collection tray may need to be placed between the bed and the blanket for collecting the fluid that is drained from the blanket. Thus, instead of being able to use the blanket right out of the package, certain preparations need to be done before the '936 blanket could be used.

As with most, if not all, of the thermal blankets that are available, in order not to impede the flow of air into the blanket, the input port of those blankets are configured to have a particular shape that oftentimes prevents the blankets from being folded to be substantially flat, thereby requiring additional space and packaging for storage and/or shipping.

SUMMARY OF THE PRESENT INVENTION

The underbody thermal convective blanket of the instant invention is adapted to be used for patients of different sizes, for example from adults to infants. The inventive blanket may be a pedi-underbody blanket when it is used for children or infants. Instead of draining fluids from the blanket, the inventive blanket is designed to minimize the evaporative and cooling effects that occur when fluids are collected onto the blanket.

To achieve this, the inventive blanket is made up of a top layer and a bottom layer joined together at their respective peripheries and at multiple locations in the form of sections. Instead of the distinct point joined locations as disclosed for the blanket of the '936 patent, at least one area where the top layer is bonded or joined to the lower layer is dimensioned at a given width, for example from 1"-3" and preferably at 2". This section extends strategically on the blanket in such a way that it does not interfere with the circulation flow of the warm air in the blanket and the air output from the top layer of the blanket, and at a location or locations on the blanket where fluids flowing onto the blanket are collected. The dimension of the section is such that at least one fluid absorbent mechanism such as a fluid absorbent pad may be secured to it for absorbing fluids that flow into that section.

Instead of securing the fluid absorbent pad on the top surface of the top or upper layer of the thermal blanket, the fluid absorbent pad may be secured to the underside of the blanket, i.e., to the exposed surface of the bottom layer. If so secured, at least one hole, or slit, is provided at the fluid collection section so that whatever fluids flow onto the section are drained directly into the pad. When the fluid absorbent pad is secured to the underside of the blanket, there is no need for such fluid absorbent pad to be confined to within the area of the section, as a relatively large fluid absorbent pad may be secured to the underside of the blanket to absorb fluids that may be drained from multiple sections. The only requirement is that different holes, apertures or slits be provided in the different sections so that whatever fluids collected in those sections are drained directly onto the fluid absorbent pad attached to the underside of the blanket.

Instead of a pad that is flat on both its top and bottom surfaces, a pad that has a flat upper surface and a corrugated lower surface may also be used. Due to the forming of multiple channels by the corrugated lower surface of such pad, the area through which fluids may pass into, and be absorbed by, the pad is increased.

For the fluid absorbent pads that are secured to the upper surface of the blanket, the top layer of the pad may be made of a hydrophobic material while the bottom surface of the pad, be it flat or corrugated, may be made of a hydrophillic material, so that the upper surface of the pad will remain dry in the event that it comes into contact with the patient. The fluids collected into the welled section are absorbed by the pad through its hydrophillic layer. To enhance absorption, only a portion of the bottom layer of the pad may be secured to the welled section of the top layer of the blanket.

So, too, the top layer of the pad may be made of a hydrophillic material while the bottom layer may be made from a hydrophobic material, so long as the patient resting on the blanket would remain substantially dry and/or not be affected by the potentially wet top surface of the pad. Further, under the same scenario, both the top and bottom layers of the pad may be made of hydrophillic material to provide a pad that is adaptable to absorb fluids from all sides.

The inventive inflatable thermal blanket onto which a subject patient is positioned therefore comprises: an air permeable top layer for receiving the subject, a bottom layer joined at its periphery to the top layer and selectively joined to the top layer at different sections to form an inflatable structure where portions of the top and bottom layers not joined form targeted areas that are inflatable, at least one input port opening into the opening of the inflatable structure, and fluid absorbent means provided to at least either the top layer or the bottom layer. Further, the fluid absorbent means may be fixedly attached to one of the joined areas or one of the joined sections at the top of the top layer that forms a well for collecting the fluids.

The invention also relates to an inflatable blanket, onto which a subject is positioned, that includes an air permeable top layer for receiving the subject, a bottom layer joined at its periphery to the top layer and selectively joined to the top layer at different sections to form an inflatable structure where portions of the top and bottom layers not joined form pocketed areas that are inflatable, at least one input port opening into the inflatable structure, at least one opening at least one of the sections to establish a through hole from the top layer through the bottom layer, and fluid absorbing means provided, either fixedly or non-fixedly, to the underside of the bottom layer of the blanket to absorb fluid drained from the top layer.

The invention further relates to a method of controlling the temperature of a subject patient that comprises the steps of: positioning the subject onto an inflatable blanket having an air permeable top layer for receiving the subject and a bottom layer joined at its periphery to the top layer and selectively joined to the top layer at different sections to form an inflatable structure where portions of the top and bottom layers not joined form pocketed areas that are inflatable, passing temperature regulated air from the top layer to the subject by inflating the structure, and providing fluid absorbent means on top of the top layer to absorb fluid from the subject or any other source.

Another invention disclosed herein relates to the input port, and more specifically the retainer provided thereat to which the air hose for inflating the blanket is mated. The retainer is a collapsible retainer that, when set to its collapsed position, configures the blanket into a substantially flat structure that may be readily folded into a neat package for shipping and storage.

To enable the retainer port to collapse to thereby allow the blanket to be folded into a substantially flat structure so as to effect a low profile blanket, the inventive input port has a retainer sheet that has at least one bent or scored line that extends along the sheet in a direction and orientation that allows the sheet to be folded along an edge of the blanket, so that once bent, the retainer sheet would fold at its bent line along the periphery of the blanket. The retainer sheet is further formed to have a seal or a plug that is removably fixed to the sheet. If the seal is not removed, air does not pass through the retainer sheet. Therefore, the input port acts as if it does not exist. To use, the retainer sheet is unfolded along its bent line so as to be flattened out. By either punching out or removing the non-permanent seal from the retainer sheet, an aperture aligned with an opening into the blanket is formed at the retainer sheet to allow the input port to accept an air hose through which temperature regulated air may be input to the blanket for inflating the same.

To enhance the straightening out or flattening of the retainer sheet from its folded or collapsible position to its input position for accepting the air hose, at least two additional bent or scored lines may be provided on the retainer sheet, possibly in parallel to but at opposite sides of the center bent line so that the retainer sheet may be folded along the two additional bent lines to form a semi box-like configuration to facilitate the insertion of the air hose into the input port of the blanket. When in its input position, the retainer sheet is substantially orthogonal to the plane where the blanket structure lies. When in its collapsed position, the retainer sheet lies substantially co-planarly with the blanket structure.

Wings may be extended from the retainer sheet, with appropriate voids or apertures thereon to enable the input port to act as an anchor for locking air hoses that are equipped with locking tabs.

The instant invention therefore also relates to a blanket comprising: a top layer, a bottom layer bonded to the top layer at least the respective peripheries of the layers to form an inflatable structure, at least one opening into the structure, and a retainer bonded to the opening adapted to accept an air input hose, wherein the retainer comprises a sheet that includes at least one bent line that extends across the sheet to enable the sheet to be folded along the one bent line so that the folded sheet would lie substantially along the plane where the blanket structure lies.

Instead of a line, the retainer sheet may have a weakened section extending therealong that allows the sheet to be folded as if there was a bent or scored line. In this instance, the invention relates to an inflatable blanket that comprises: a top layer and a bottom layer bonded together at least their respective peripheries to form an inflatable structure, at least one opening into the structure and a retainer bonded to the opening adapted to accept an input air hose. The retainer comprises a sheet that includes one weakened section extending longitudinally along the length of the sheet so as to allow the sheet to lie substantially co-planarly with the blanket structure when the sheet is folded along the one weakened section, and to lie substantially orthogonal to the blanket structure when the sheet is not folded along the weakened section.

BRIEF DESCRIPTION OF THE FIGURES

The present invention will become apparent and will best be understood by reference to the following description of the invention taken in conjunction with the accompanying drawings, wherein:

FIG. 3 is a cross-sectional view of a different embodiment of a fluid absorbent pad secured to a bonded section of the inventive thermal blanket;

FIG. 4 is a third embodiment illustrating a fluid absorbent pad secured to the underside of a thermal blanket;

FIG. 7 is a perspective view illustrating the relationship of an air hose and the retainer sheet of the instant invention;

FIG. 8 is a side view showing the mating of an air hose to the retainer sheet of the instant invention;

DETAILED DESCRIPTION OF THE INVENTION

Figure 1:
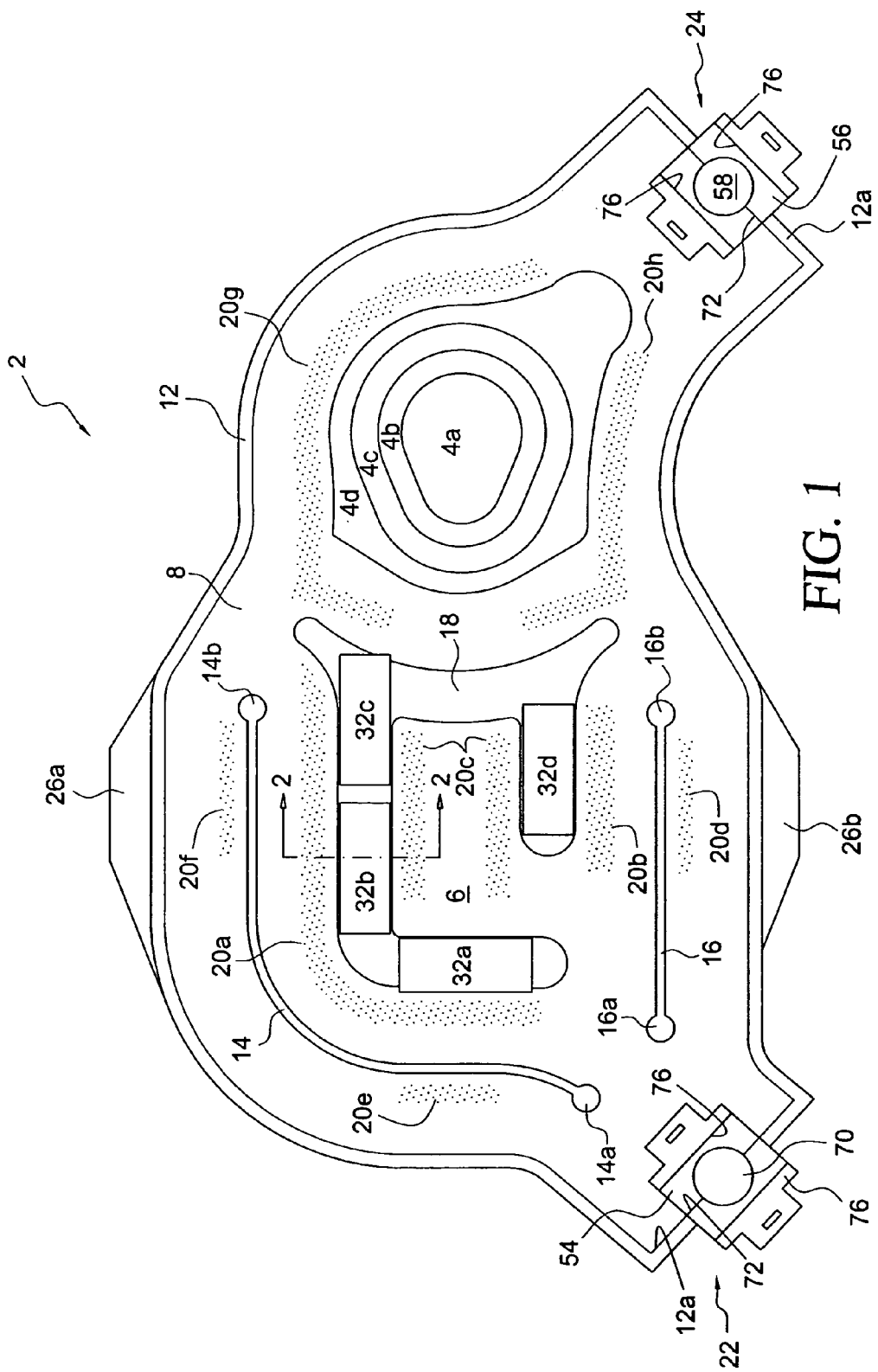
FIG. 1 is a top view of an inflatable convective thermal blanket of the instant invention.
Figure 2:
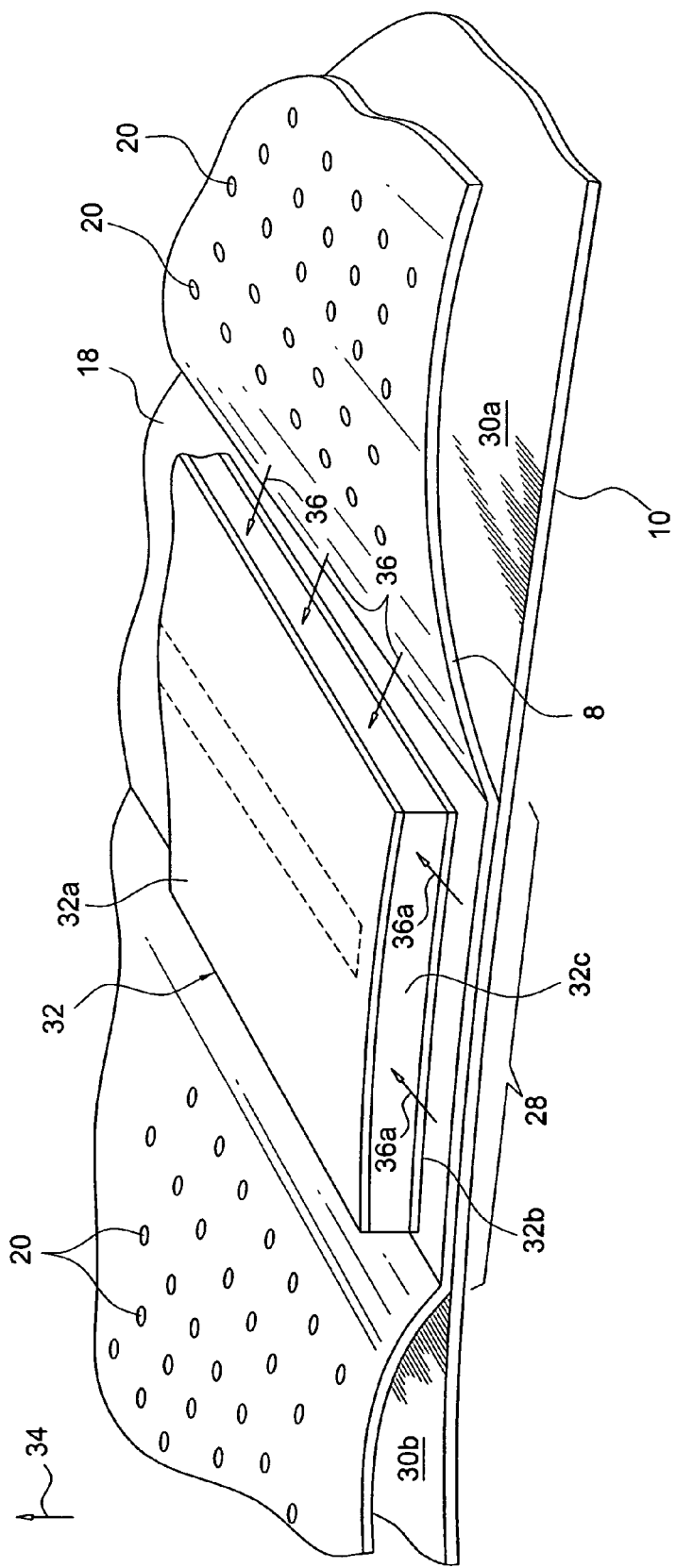
FIG. 2 is a semi-perspective cross-sectional view of a section of the blanket with a fluid absorbent pad secured thereto.

With reference to FIG. 1, an inflatable convective thermal blanket 2 is shown to have a structure that is configured to have a head portion 4 and a body portion 6 onto which a subject patient, such as for example an infant, may be placed. The patient is supported by the upper or top layer 8, as shown in FIG. 2, which is joined to a lower or bottom layer 10 at the respective peripheries 12 of the top and bottom layers. Top layer 8 is further joined to bottom layer 10 at different locations or sections such as for example 14 and 16. In addition, for the inventive blanket, an exemplar section 18 that has a wider dimension than those of sections 14 and 16 joins top layer 8 to bottom layer 10. For the inventive blanket, sections 14 and 16 each are formed in a particular configuration, with the respective ends of each of the sections shown to have a circular end point configuration. These circular end points, which may also be of some other configurations, provide strain relief for these sections. Thus, section end stops 14a and 14b provide strain relief for section 14. The same is true with respect to section 16 in which end stops 16a and 16b likewise provide strain relief for section 16.

For those portions of the blanket that are not joined, pocketed areas that inflate when air is input to the blanket are formed. Some of those areas of the blanket include a plurality of holes 20 through which temperature regulated air in the blanket could be directed to and thereby regulate the temperature of the patient. As shown, sets of holes 20a and 20b are provided about section 8, while sets of holes 20c are provided in the pocketed area surrounded by section 18. In addition, there are a plurality of sets of holes 20d, 20e and 20f provided at top layer 8 adjacent to sections 14 and 16. Moreover, two sets of holes 20g and 20h are provided around the head section 4 of the blanket. Note however that the instant invention blanket is not limited to the configuration of holes as shown in FIG. 1, nor for that matter the configuration of the sections shown. The important thing for the inventive blanket is that there be at least one section, aside from the periphery of the blanket, to which the top layer 8 is joined to the bottom layer 10. Further, in order that the blanket can support a subject patient such as an infant, the blanket is designed to have a head portion and a body portion. For some patients, however, the head portion may not be needed, as the body portion may well be extended lengthwise to provide support for the head of the adult patient.

So that the head of the patient remains still when placed on the blanket, for the embodiment shown in FIG. 1, head section 4 is made up of a number of concentric sections with central head section 4a being surrounded by sections 4b, 4c and 4d. In the event that it is not desirable to input air to the head portion of the blanket, top layer 8 is joined or bonded to bottom layer 10 of the blanket at head sections 4b and 4d, so that there is no air input to head portion 4 of the blanket.

Blanket 2 is designed to be inflated with the patient resting thereon. Further, blanket 2 is designed to ensure that fluids from the patient, or another source(s), would not affect substantially the temperature of the patient. To that end, the inventors have found that by designing the blanket to have at least one section of a given dimension and by placing or securing to that section fluid absorbent means, fluids from the patient or some other source will be absorbed by the fluid absorbent means, so that the temperature of the patient, as regulated by the blanket, would not be substantially adversely affected by the presence of the fluid. Thus, the inventive blanket 2 is designed to minimize the evaporative and cooling effects fluids collected on the blanket may have on a subject patient.

For the inventive blanket, the top and bottom layers each may be made from a 0.9 oz./sq. yd., white non-woven spun-bound polypropylene material. Both the top layer 8 and the bottom layer 10 may have extrusion coating thereon a white low density polyethylene coating to prevent fluid from passing through. The top layer 8 is an air permeable layer due to holes effected thereon.

As further shown in FIG. 1, blanket 2 has a number of input ports, for example 22 and 24 at the leg and head portions, respectively. Each of those input ports 22 and 24 is the same. The important thing to note is that only one of those ports needs to be used at any given time. The discussion relating to the input ports 22 and 24 will be given, infra, with respect to the inventive retainer mechanism that is a part of each of the input ports. Even though there are only two input ports shown in the FIG. 1 embodiment, at least one or additional input ports may conceivably be provided to inflation thermal blankets such as blanket 2 shown in FIG. 1.

Flaps 26a and 26b are extensions of blanket 2 which may be used for placing or more securely mounting blanket 2 onto a table or bed.

With reference to FIG. 2, which shows section 2-2 of FIG. 1, as discussed previously, upper layer 8 is joined to bottom layer 10 to form a section 18. For the inventive blanket, section 18 may be configured to have a width, as indicated by designation 28, that may be anywhere from 0.5" to approximately 4". For the preferred embodiment, section 18 has a width 28 of approximately 2". Further as discussed previously, at those portions of the blanket where upper layer 8 is not joined to bottom layer 10, pocketed areas such as 30a and 30b, as shown in FIG. 2, are formed. Temperature regulated air input to the blanket would escape from the air permeable upper layer 8 through those air pockets 30. To enhance the output of air, strategically placed holes 20 are provided at upper layer 8 to direct the temperature regulated air to the patient, who is lying on top of blanket 2.

As further shown in FIG. 2, an exemplar fluid absorbent pad 32 is secured to the top surface of top layer 8, at section 18. Absorbent pad 32, for the embodiment shown, includes a top surface layer 32a, a bottom surface layer 32b and a middle layer 32c sandwiched by top layer 32a and bottom layer 32b. Top and bottom layers 32a and 32b may also be considered as covers for layer 32c. To ensure that the patient does not come into contact with a wet surface, top layer 32a of pad 32 may comprise a sheet of hydrophobic material that may be made of a white non-woven spun-bound polypropylene material that has extrusion coated at one side a low-density polyethylene coating. The bottom layer 32c of pad 32, on the other hand, may comprise a non-woven spun-bound polypropylene material that is uncoated. In other words, bottom layer 32c of pad 32 may be a hydrophillic material that is adapted to absorb fluids. The layer 32c of the material sandwiched by top layer 32a and bottom layer 32c of pad 32 is a fluid absorbent material that may include, for example, cotton, other fibrous materials, or a material made of high performance cellulose fibers and a super absorbent polymer (SAP). One such exemplar cellulose fibers and absorbent polymers material that may be used for layer 32c of fluid absorbent pad 32 is the NovaThin absorbent core made by the Rayonier Inc., which has its United States headquarters at Jacksonville, Fla. Fluid absorbent pad 32 may be secured to section 18 by adhesion, for example using an adhesive including for example a non-fluid affected glue and/or adhesive strips.

Although the exemplar fluid absorbent pad 32 shown in FIG. 2 is disclosed to have a hydrophobic top layer and a hydrophilic bottom layer, it should be appreciated that in practice the converse configuration may be used, i.e., the top layer being a hydrophilic and the bottom layer being hydrophobic. Moreover, so long as the patient resting on the blanket would remain substantially dry and/or not be affected the fluid absorbent pad (for example when the inflated portions of the blanket raise the body of the patient high enough off the padded section so that the patient does not come into contact with the top layer of the fluid absorbent pad), both the top and bottom layers or surfaces of the fluid absorbent pad may be made of hydrophilic material so that fluids may be absorbed by the fluid absorbent pad at any angle, or from all sides.

When blanket 2 is inflated, given that upper layer 8 would tend to extend in the direction as indicated by directional arrow 34, and that section 18 is lower than the inflated portions of the blanket, fluids from the patient, and other sources, are collected in the valley or well established by section 18. These fluids are then absorbed by absorbent pad 32 in the direction as indicated by directional arrows 36, i.e., at the different sides of portion 32c, as well as by bottom layer 32b. Even though all four sides of pad 32 are shown to be opened to layer 32c, in practice, top layer 32a may be joined directly to bottom layer 32b at their respective edges, similar to a sealed package for example, so that fluids seep into and be absorbed by portion 32c of the pad through the hydrophillic bottom layer 32b. Alternatively, the non-longitudinal sides of the pad 32 may not be sealed, so that fluids may readily be absorbed by layer 32c via the cross sectional sides of pad 32, per shown by directional arrows 36a in FIG. 2. So, too, if the thickness of pad 32 vis-a vis the inflated portions of blanket 2 is such that the patient being supported by blanket 2 does not come into contact with the top surface of pad 32, then pad 32 may be configured to have a hydrophilic top layer 32a in addition to a hydrophilic lower layer 32b, so that fluids may also be absorbed by pad 32 through its top layer 32a.

FIG. 3 illustrates a different type of fluid absorbent pad that may be used for enhancing the fluid absorbability of the inventive blanket. Components in FIG. 3 that are the same as in FIGS. 1 and 2 are numbered the same. In particular, fluid absorbent pad 38 of the FIG. 3 embodiment is also secured to section 18 of the inventive blanket. Instead of the substantially rectangular shaped pad 32 shown in FIG. 2, fluid absorbent pad 38 is a "gusset" like pad that has a top layer 38a and a lower layer 38b that extends to top layer 38a by way of two sides 38b'. As shown, lower layer 38b of pad 38 has a corrugated shape so that multiple channels or grooves, such as for example channels 40a-40d, may be formed between the bottom surface of bottom layer 38b of pad 38 and the top surface of top layer 8 of the blanket. Same as the earlier embodiment, top layer 38a may be made from a hydrophobic material that maintains its dryness while bottom layer 38b may be made from a hydrophillic material that allows fluids to pass through. Alternatively, top layer 38a may be hydrophilic while bottom layer 38b may be hydrophobic, or both top layer 38a and bottom layer 38b may be hydrophilic.

Enclosed by layers 38a and 38b is the fluid absorbent material mentioned earlier, for example the high performance cellulose fibers and super absorbent polymer (SAP) material NovaThin, that effectively absorbs fluids that may be collected on section 18 of the blanket. Pad 38 is attached or secured to top layer 8 of the blanket by any one or more of the contact points 42 shown. Thus, given that bottom layer 38b provides a corrugated surface, the surface area adapted to be exposed to fluids is therefore increased for the fluid absorbent pad 38 of the FIG. 3 embodiment. That being the case, fluid absorbent pad 38 may be able to absorb fluids at a faster rate than the pad shown in FIG. 2. Fluids are shown to be absorbed by layer 38c through layer 38b per directional arrows 39.

FIG. 4 shows yet another embodiment of the fluid absorbent pad of the instant invention. As before, the components for the FIG. 4 embodiment that are the same as in the previously discussed embodiments are labeled the same. For the embodiment of FIG. 4, instead of securing the fluid absorbent means such as a fluid absorbent pad on the top of upper layer 8 of the blanket, the fluid absorbent means is secured to the lower surface of bottom layer 10 of the blanket. As shown, fluid absorbent pad 44 is securely attached to bottom layer 10 by some portions of its top layer 44a, which is joined to its enclosure layer 44b. For fluid absorbing pad 44, layer 44a is a hydrophillic layer through which fluid may pass and be absorbed by the material in layer 44c of the pad. Alternatively, the portion of top layer 44a, designated 44a' may be removed from layer 44a so that fluids collected on section 18 may flow directly into material 44c of pad 44. To enhance the draining of fluid into fluid absorbent pad 44, a number of openings or slits such as 46a to 46c may be effected on section 18. As before, layer 44c of pad 44 may be a material such as the above mentioned NovaThin. For the FIG. 4 embodiment, therefore, instead of absorbing the fluid directly on the well area created by section 18, the collected fluids are drained to a fluid absorbing material that is mounted to the underside of the blanket. Note that even though pad 44 is exaggeratedly shown to be thicker and covers only a bit more area than section 18, in practice, pad 44 may be a much thinner pad that extends across a major portion, if not all, of bottom layer 10 of the blanket.

There may be a plurality of fluid absorbent means securely attached to section 18 and/or some other sections, be those means the pad 32 shown in the FIG. 2 embedment or the pad 38 shown in the FIG. 3 embodiment. This is illustrated in FIG. 1 where a plurality of fluid absorbent pads, designated for example by 32a-32d, are separately mounted to section 18 on top layer 8 of blanket 2. Although a plurality of fluid absorbent pads are shown, it should be appreciated that section 18 could be filled completely with the types of fluid absorbent materials as described above; or, alternatively, a greater or lesser number of pads than that shown in FIG. 1 may be secured to section 18, and/or some other similarly dimensioned sections of the blanket.

Moreover, although shown to be located at the body portion 6 of blanket 2, section 18, or some other section(s), may in fact be extended towards, or provided at head portion 4 of blanket 2, with the appropriate fluid absorbent pad(s) added thereon. Furthermore, instead of a single section such as 18 shown in FIG. 1, a number of separate non-contacting sections similar to section 18 may be provided onto the inventive blanket, so long as those sections are dimensioned in accordance as discussed above, so that the appropriate fluid absorbent material may be secured or mounted thereon for absorbing fluids from the patient or other sources that may be collected at those welled sections of the blanket. As for the embodiment shown in FIG. 4, different sections, with appropriate holes or slits effected thereon, may be formed on the blanket to provide fluid paths whereby fluids may be drained from the different sections onto the fluid absorbent pad secured to the back or underside of the blanket.

A second invention is disclosed by FIGS. 5-10. Components in FIGS. 5-10 that are the same as those discussed in FIGS. 1-4 are labeled the same.

Figure 5:
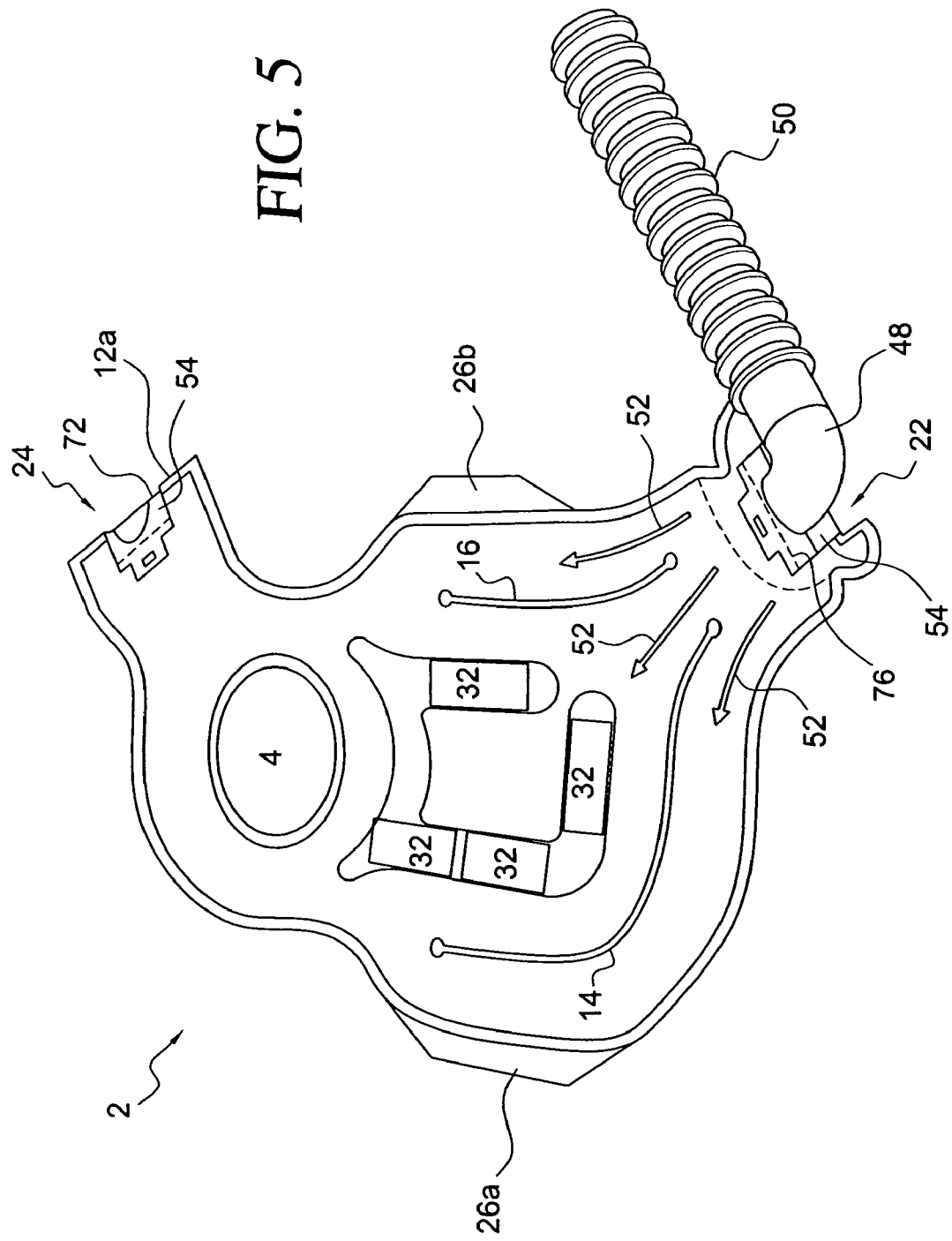
FIG. 5 shows the thermal blanket of the instant invention with an inventive input port for mating with an air hose.

As shown in FIG. 5, input port 22 of blanket 2 is mated to an air hose 48, which in turn is connected by a tubing 50 to an air blower, not shown, as is well known. Also well known is that temperature regulated air, such as warmed air, is input to blanket 2, per indicated by the directional arrows 52. Input port 24 is shown not being used in FIG. 5.

Figure 6:
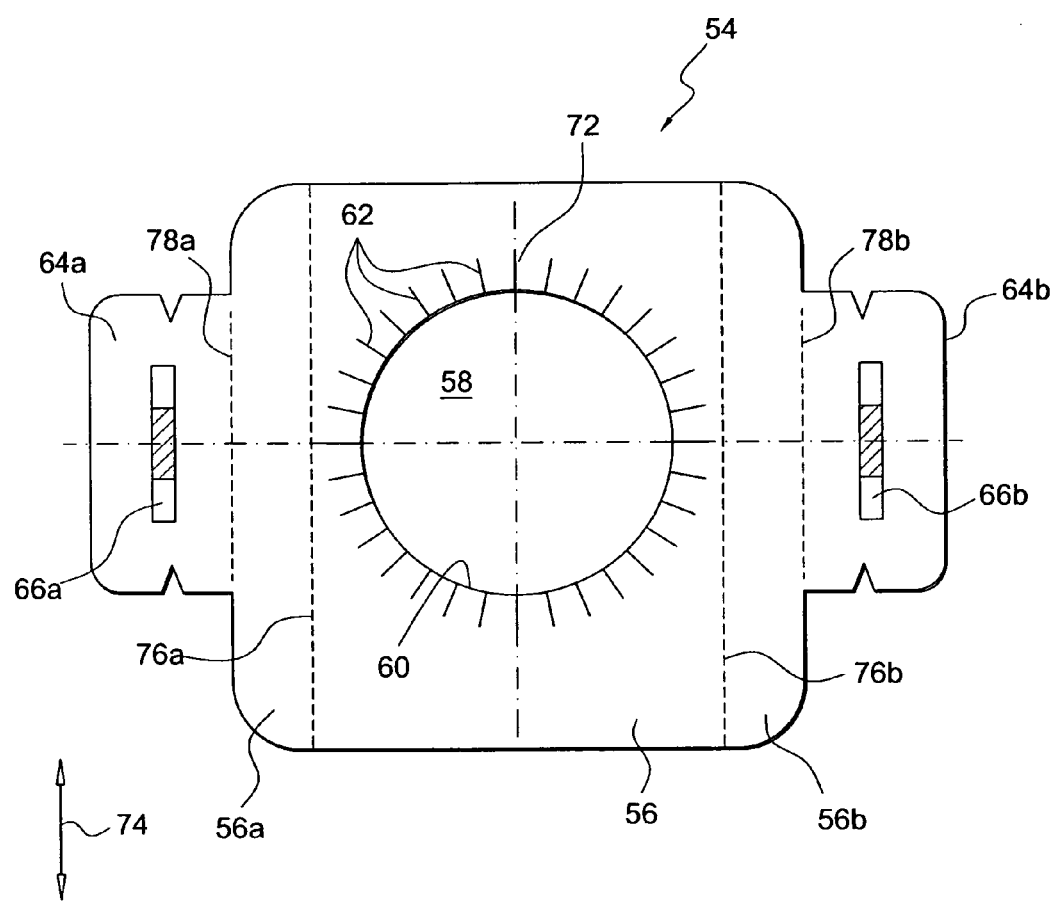
FIG. 6 is a plan view of the inventive retainer sheet of the instant invention.

With reference to FIGS. 1 and 5 and with particular reference to FIG. 6, note that each of the input ports 22, 24 is fitted with a retainer sheet 54. Sheet 54 may be made of a medical grade cardboard, or plastic, or some other material that would afford flexibility and bendability. As shown, sheet 54 has a main body 56 that has a center portion 58 that is removably attached to main portion 56 by a continuous circular cut line 60 and a plurality of smaller cut lines 62 that extend outwards from circular cut line 60. For the FIG. 6 embodiment, although not critical to the invention, two wings 64a and 64b extend opposedly from body 56 of sheet 54. Each of the wings 64a, 64b has a slot 66a, 66b, respectively, which are used for attachment with corresponding locking tabs, such as tabs 68, that are mounted to an air hose 48. See FIG. 10. Sheet 54 is dimensioned to enable it to be attached or bonded to an opening of the blanket, identified as 70 in FIG. 1 for example, so that when center portion 58 is removed from sheet 54, opening 70 provides an entry whereby air may be input to the blanket. Sheet 54, as it is used with the input opening of blanket 2, may be referred to as the retainer sheet.

As best shown in FIG. 6, retainer sheet 54 has a central bent or scored line 72 that extends longitudinally in the direction as indicated by directional arrows 74 across body 56, including across removable portion 58. Bent line 72 allows sheet 54 to be bent or folded, as indicated by sheet 54 at the input port 24 shown in FIG. 5. Two additional bent or scored lines 76a and 76b, each running parallel to but at either side of line 72, also extend across body 56 along the direction indicated by directional arrows 74. Bent lines 76a and 76b provide sheet 54 with the flexibility of being bent or folded into a semi-boxlike configuration, such as that shown by sheet 54 at input port 22 of FIG. 5, so that the retainer sheet 54 is positioned substantially orthogonal to the plane where the structure of blanket 2 lies.

On the other hand, as shown by the retainer sheet 54 at port 24, inasmuch as there is no need for an air hose to be inserted at that input port, retainer sheet 54 remains folded, or in its collapsed position, so that it remains in a substantially coplanar relationship with the blanket structure, i.e., it lies closer to or substantially along the same plane as the blanket. Thus, by unfolding sheet 54, from the position shown at input port 24 to the position shown at input port 22 of FIG. 5, and by further folding sheet 54 at lines 76a, 76b so that portions 56a and 56b of body 56 are folded substantially at right angle relative to main body 56, a semi-boxlike shape that conforms sheet 54 to be better adapted to receive air hose 48 can be effected. To enable wings 64 to be folded so that slots 66 may be engaged with respective locking tabs 68 shown in FIG. 10, additional bent or scored lines 78a and 78b are provided at the corresponding junctions where wings 64a and 64b, respectively, extend from body 56 of retainer sheet 54.

The placement of retainer sheet 54 onto blanket 2 to form the input port, for example input port 24 shown in FIG. 5, is done such that retainer sheet 54 may be folded or collapsed, along with blanket 2, into a substantially flat shape for storage or shipping purposes. To best achieve this desired collapsibility, retainer sheet 54 is bonded to the periphery of the blanket, such as at periphery 12, so that retainer sheet 54 may be bent at bent line 72, which is shown to be flush with periphery portion 12a in FIGS. 1 and 5.

Although the sections where sheet 54 are foldable are referred to as bent lines or scored lines above, it should be appreciated that those bent or scored lines may actually be weakened sections that similarly would allow sheet 54 to be bent or folded, per the above discussion.

FIG. 7 shows in perspective view the hose retainer sheet 54, in relation to air hose 48, after portion 58 has been removed from sheet 54, and after sheet 54 has been unfolded into the position that is substantially orthogonal to the plane of the blanket, so that air hose 48 may readily be inserted into opening 70. With the cut lines 62 provided on body 56, the insertion of hose 48 into opening 70 of the blanket is facilitated, as opening 70 may be widened, per the bending of the cut lines 62 for accepting portion 48a and barb 48b of air hose 48. As barb 48b has a larger diameter than entry portion 48a, once barb 48b enters and passes the lip of opening 70, due to the shape of opening 70 being affected by the cut lines 62, air hose 48 is securely mated to retainer sheet 54, and therefore the input port of the blanket. Only with a predetermined force would air hose 48 be removed from opening 70. An outer ring 48c at the top portion of air hose 48 prevents the air hose from being inserted further than necessary into opening 70.

FIG. 8 shows air hose 48 having been properly mated to hose retainer sheet 54.

Figure 9:
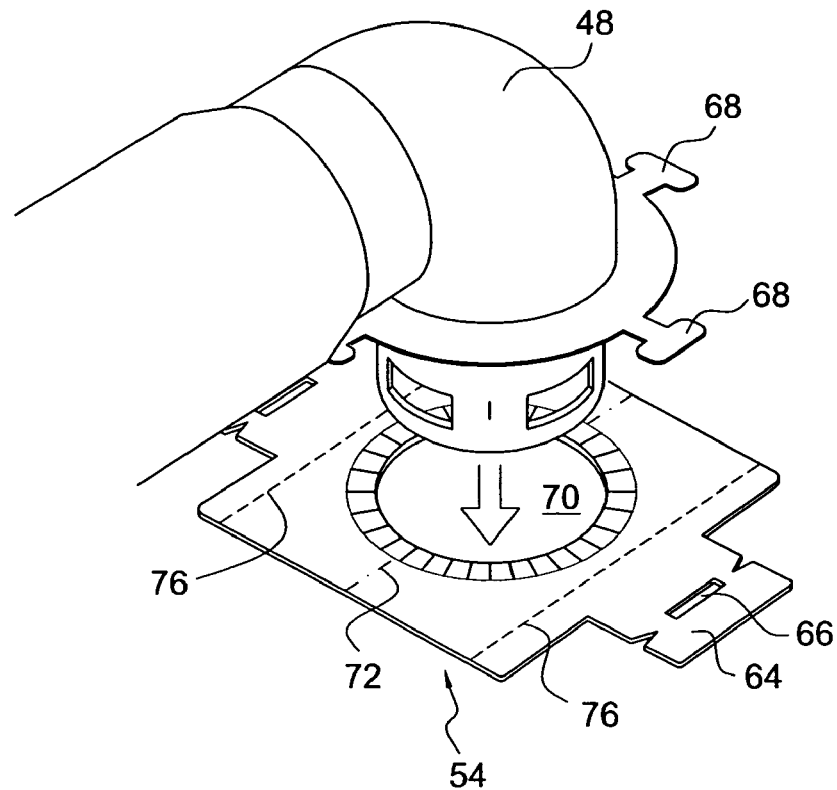
FIG. 9 is a perspective view illustrating another type of air hose relative to the retainer sheet of the instant invention.

FIG. 9 illustrates an air hose 48 that is fitted with locking tabs 68 that are engagable with slots 66 of hose retainer 54.

Figure 10:
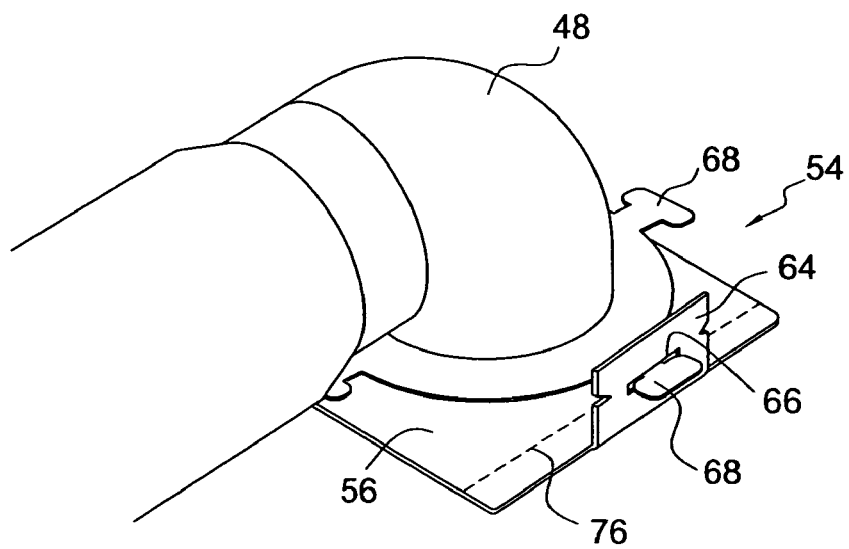
FIG. 10 shows the coupling of the air hose of FIG. 9 to the retainer sheet of the instant invention.

FIG. 10 shows the mating of air hose 48 to hose retainer 54, and the locking of tabs 68 to slot 66 of one of the wings 64, as was discussed above.

The inventions as disclosed above are subject to many variations, modifications and changes in detail. Thus, it is intended that all matters described throughout this specification and shown in the accompanying drawings be interpreted as illustrative only and not in a limiting sense. Accordingly, it is intended that the inventions be limited only by the spirit and scope of the hereto appended claims.

The invention claimed is:

1. A method of manufacturing an inflatable blanket, comprising the steps of:
   bonding a top layer and a bottom layer together at least at their respective peripheries to form an inflatable structure;
   establishing at least one opening into said structure;
   bonding a retainer adapted to accept an input air hose to the opening, said retainer comprising a sheet that attaches to the opening to close the opening, said sheet having a center portion defined by a continuous cut line; and
   effecting at least one weakened section longitudinally extending across the length of said retainer to enable said retainer to lie substantially coplanarly with said structure when said retainer is folded along the weakened section, and to lie substantially orthogonal to said structure when said retainer is not folded along the weakened section.

2. Method of claim 1, further comprising the step of:
   defining the center portion defined by the continuos cut line as a non-permanent seal removable from said sheet so as to expose the opening.

3. Method of claim 1, further comprising the steps of:
   forming two other weakened sections along said retainer in parallel to said one weakened section; and
   configuring said retainer into a shape better adapted to receive said hose by unfolding said retainer along said one weakened section and bending said retainer along said other weakened sections.

4. Method of claim 1, further comprising the step of:
   aligning said one weakened section along a section of a periphery of said structure so that once said sheet is folded along said one weakened section, the folded edge of said sheet is flush with the periphery section of said structure.

5. Method of claim 1, further comprising the step of:
   forming at said sheet at least one wing bendable along another bent line at right angle relative to said sheet that includes a slot to enable a hose equipped with an attachment barb to be securely attached to said retainer.

6. Method of claim 1, further comprising the step of:
   making said sheet from cardboard or plastic.

7. A method of making a blanket comprising the steps of:
   bonding a top layer to a bottom layer at least the respective peripheries of the layers to form an inflatable structure;
   forming at least one opening into said structure; and
   bonding a retainer to the opening to accept an air input hose, wherein said retainer comprises a sheet that includes a center portion that is a part of said sheet, said center portion being defined by a cut line that enables said center portion to be removable from said sheet, said center portion being positioned in alignment with the opening, said retainer having at least one bent line extending across said sheet including across said center portion to enable said sheet and said center portion to be folded along said one bent line so that the folded sheet including said center portion would lie closer to or substantially along the plane where said structure lies.

8. Method of claim 7, wherein said sheet, when unfolded, lies in a plane that is substantially orthogonal to the plane of said structure.

9. Method of claim 7, wherein after removal of said center portion from said sheet, said hose is insertable into the opening of said structure.

10. Method of claim 7, further comprising the step of:
forming at said sheet at least one wing bendable along another bent line at right angle relative to said sheet that includes a slot to enable a hose equipped with an attachment barb to be securely attached to said retainer.

11. Method of claim 7, further comprising the step of:
forming two additional bent lines extending parallel to and along either side of said one bent line, wherein when said sheet is not folded along said one bent line, said sheet may be folded along each of the additional bent lines to configure said retainer to a shape better adapted to receive said hose.

12. Method of claim 7, further comprising the step of:
making said sheet form cardboard or plastic.

13. A method of manufacturing a thermal inflatable blanket, comprising the steps of:
bonding a top layer and a bottom layer together at least at their respective peripheries to form an inflatable structure; and
forming an input port into said structure, said input port including a retainer having a main body and a seal that is a part of said retainer but is removable from the main body of said retainer to accept an input air hose, said retainer including one bent line longitudinally extending across the length of the main body and the seal and two other bent lines each running parallel along but at respective sides of said one bent line, said retainer collapsible to lie substantially coplanarly with said structure when folded along said one bent line, and to lie substantially orthogonal to said structure when not folded along said one bent line.

14. Method of claim 13, further comprising the steps of:
closing the opening of said inlet port with said seal; and
defining said seal by a cut line on said retainer so that said seal is readily removable from said retainer.

15. Method of claim 13, wherein when said retainer is not folded along said one bent line, the method further comprising the step of:
respectively folding said retainer along said other bent lines so as to configure said retainer into a shape better adaptable to receive said hose.

16. Method of claim 13, further comprising the step of:
making said sheet from cardboard or plastic.

* * * * *